(12) United States Patent
Kordis et al.

(10) Patent No.: US 6,699,268 B2
(45) Date of Patent: Mar. 2, 2004

(54) RADIO FREQUENCY PATIENT HEATING SYSTEM

(75) Inventors: Thomas F. Kordis, Wilmington, MA (US); Mark E. Whitebook, Capistrano Beach, CA (US); Scott M. Evans, Santa Ana, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 10/013,166

(22) Filed: Dec. 10, 2001

(65) Prior Publication Data
US 2002/0077665 A1 Jun. 20, 2002

Related U.S. Application Data

(60) Provisional application No. 60/256,090, filed on Dec. 15, 2000.

(51) Int. Cl.[7] .................................................. A61F 7/00
(52) U.S. Cl. ........................ 607/105; 607/106; 607/113
(58) Field of Search ............................ 607/96, 98, 99, 607/101, 102, 113, 122; 606/27, 28, 29, 31, 32, 33, 41, 42

(56) References Cited

U.S. PATENT DOCUMENTS

| | | | | |
|---|---|---|---|---|
| 5,188,602 A | * | 2/1993 | Nichols | 604/113 |
| 5,681,280 A | * | 10/1997 | Rusk et al. | 604/96.01 |
| 5,997,571 A | * | 12/1999 | Farr et al. | 607/92 |

* cited by examiner

Primary Examiner—Roy D. Gibson
(74) Attorney, Agent, or Firm—John L. Rogitz

(57) ABSTRACT

The system of the present invention includes a heat exchange catheter for warming flowing blood within a blood vessel. The heat exchange catheter includes a catheter body having a proximal end and a distal end with electrodes. The electrodes generate an electric field that radiates heat to the flowing blood. The electrodes comprise discrete bands that serially align and are spaced apart from each other. Each electrode has a polarity, and for each electrode there is an adjacent electrode having an opposite polarity. A support centrally aligns the catheter body within the blood vessel.

6 Claims, 5 Drawing Sheets

RADIO FREQUENCY PATIENT HEATING SYSTEM

PRIORITY

Priority of application Ser. No. 60/256,090 filed on Dec. 15, 2000 in the United States of America with the USPTO is claimed under 35 U.S.C. §119(e).

FIELD

This invention relates to devices and methods for transferring thermal energy to a patient, and more particularly vascular catheters and systems for dispelling hypothermia.

BACKGROUND

It is common for patients surgical procedures, to experience mild to severe hypothermia. There are numerous causes for this decrease of body temperature. One cause pertains to anesthesia. Anesthesia may depress the body's set-point temperature as regulated by the brain's thermal control center.

Another cause for decreased body temperature during surgery may manifest when the patient has his or her thoracic or abdominal cavity opened. This greatly increases the amount of surface area exposed to the atmosphere and thereby accelerates loss of body heat. As a rule, surgical suites are kept very cool. Cool surgical suites can make patients cold.

Several surgical procedures (e.g., coronary bypass grafts, valve replacements, etc.) utilize intentional hypothermia in order to decrease the body's energy demands during the procedure. These patients need to return from a deep hypothermic state to a normal body temperature following the procedure.

Current methods of treating the hypothermic patient include hot baths, delivering warm fluids orally and applying heating blankets. Heating blankets use either air or liquid as the heat-transfer medium. If placed below the patient, a heating blanket transfers thermal energy to the patient by a combination of conduction and convection. Conductive heating results from intimate, pressured, contact with the skin of a patient. Convective heating results from using a local air film between the blanket surface and a patient's skin to convectively heat the patient.

Some air type heating blankets are placed over the patient, and supply warm air under low pressure via the blanket. The warm air "leaks" out of the blanket at low velocity and with reasonable uniformity over its surface to warm the patient. Heating blankets transfer heat through the patient's skin surface, relying principally on the vascular system to transfer the thermal energy to the patient's core via the blood flow.

The rate of heat transfer, and therefore the effectiveness, of a heat-blanket warming system is limited by the body's natural response to low core temperatures. Such a response may include "shutting down" blood flow to the extremities. The body may also sweat in response to application of a heating blanket. Sweating cools the body and reduces the effectiveness of heating blankets.

The heating blanket approach is sometimes used in conjunction with other ways of heating the patient, such as heating the blood supply directly. U.S. Pat. No. 5,837,003 to Ginsburg, issued Nov. 17, 1998, discloses an exemplary way of using an electrically resistive heater at the end of a catheter to heat the blood supply of a patient. Heating the blood supply, in conjunction with blankets and other ways of heating the patient, can shorten the time required to bring a patient to normothermia.

One drawback to the invention disclosed by Ginsburg is that in order to transfer a significant amount of heat to the blood supply, the resistive element would have to be very hot. It is known, however, that blood heated over 42 degrees C., or so, may coagulate. Accordingly, the maximum temperature at which the resistive elements operate is restricted by the tendency of the blood to coagulate.

In an effort to provide a catheter that can transfer heat at relatively lower temperatures, the catheter surface area has been increased. One design increases the distal diameter of the catheter (See U.S. Pat. No. 5,837,003 FIG. 7). Other designs show helical fins, annular fins and axial fins, respectively. (U.S. Pat. No. 5,837,003 FIGS. 8a, 8b, and 8c). The fins maximize the surface area of the catheter in contact with the blood supply and, thereby, improve the ability of the catheter to conduct heat to the blood supply.

Maximizing the area of a heating surface on a catheter is not wholly effective. One reason for this is that increasing the diameter of a catheter impedes blood flow, which, may reduce the effectiveness of any heat transfer between the catheter and the blood supply. Further, fins may impede blood flow in regions adjacent the fins, causing the blood to overheat. Blood that overheats could coagulate on the fins.

Fins, by themselves, are somewhat inefficient. Much of the blood that passes the catheter does not contact the fins or heat exchange elements and therefore, may not undergo a significant temperature change.

What is desired is a catheter that does not significantly impede blood flow. What is also desired is a catheter with improved heat transfer capability without overheating the blood.

SUMMARY

The system of the present invention includes a heat exchange catheter for warming flowing blood within a blood vessel, or for warming tissue in any body cavity. The heat exchange catheter includes a catheter body having a proximal end and a distal end with electrodes and temperature sensor elements.

The electrodes generate an electric field that radiates into the flowing blood. Heating of the blood results when the electric field exerts one of two possible effects on the blood, depending on the frequency of the energy and whether the electrodes are in direct ohmic contact with the blood.

It is understood that the electric field accelerates free electrons in the blood, creating a flow of localized electric currents in the blood. The electric currents flowing through the blood cause resistive heating of the fluid through the relationship $P=I^2R$, where P is power, I is the RMS current and R is the blood resistance.

It is also understood that the electric field is absorbed, principally by the water molecules that make up the bulk of the blood volume. Dielectric loss in the water molecules converts the electric field energy to thermal energy.

The electrodes comprise discrete bands that serially align and space apart from each other. Each electrode has a polarity, and for each electrode there is an adjacent electrode having an opposite polarity. The electric field is generated between the electrodes of opposing polarities, and the electric field extends radially out from the bands to heat flowing blood.

While the electric field is used to heat the blood, it is envisioned that additional forms of heating can be used in conjunction with the heating method of the present invention such as having resistive heating elements in or on the catheter, and having a circulating heating fluid within the catheter.

The system includes a control unit coupled with the catheter via electric cabling for powering the electrodes with radio frequency (RF) energy. The control unit provides alternating current to the electrodes in the RF frequency range (i.e., between 100 kHz to 3,000 kHz). Preferably, the current is at about 500 kHz to generate an electric field of a corresponding frequency.

To optimize the heating effects of the electrodes, the catheter includes a selectively deployable support for positioning the electrodes centrally within the blood vessel. Ideally the support gently holds the catheter within the blood vessel by gently pressing against the walls of the blood vessel. Central positioning of the catheter optimizes heat exchange between the catheter and the blood. The support, according to one aspect of the invention, is adjustable in length.

The support is described in terms of multiple possible embodiments. A according to one embodiment the catheter has multiple supports comprising flattened wires having ends and lengths. The ends of the supports attach to the catheter body. The lengths align longitudinally along the catheter body to selectively deploy against the blood vessel wall to center the catheter body within the blood vessel. Preferably, the distal end of the catheter body includes a switch mechanically coupled with the supports to selectively deploy the supports. Alternately, automatically deployable supports are provided that deploy in response to removal of an insertion tube, or similar device.

Variations of this embodiment include an aspect having the ends of the supports attaching to the catheter body in a position proximal the electrodes. Another aspect has the supports attaching to the catheter body in a position distal the electrodes. Yet another aspect has one end of each support attaching to the catheter body in a position proximal the electrodes, and the other end of each support attaching to the catheter body distal the electrodes.

According to another embodiment, the supports have pins that radially extend from the catheter body to bear gently against the blood vessel.

According to another embodiment, each support includes a ring and extensions. The extensions support the ring to selectively deploy the ring from a first configuration where the ring lies flush along the catheter body to a second configuration where the ring gently presses against the blood vessel. The extensions and ring cooperate to permit blood to flow past the extensions when the ring holds the catheter body centrally within the blood vessel. According to one aspect of this embodiment, the extensions extend at an oblique angle from the catheter body to the ring so that the extensions and the ring form a frustum shape.

One aspect of this embodiment manifests where the ring and extensions form a web. The web circumscribes the catheter body, the web being selectively deployable from a first configuration where the web lies on the catheter body, to a second configuration where the web extends from the catheter body to the blood vessel. The web permits blood to flow through the web when the web holds the catheter body centrally within the blood vessel. The web achieves a frustum shape in the second configuration, according to a variation of the invention. According to a further variation, the web comprises a resistive heating elements which conducts RF current and cooperate with the electrodes to warm the blood.

According to yet another embodiment, the blood vessel has a wall and the support includes a helical wire for contacting the wall of the blood vessel along a helical path. The helical wire is distanced from the distal end of the catheter body to facilitate blood flow between the helical wire and the catheter.

BRIEF DESCRIPTION OF THE DRAWINGS

The invention is described in terms of various embodiments, reflected in the figures, wherein like parts have like reference numerals, and wherein.

DETAILED DESCRIPTION

Figure 1:
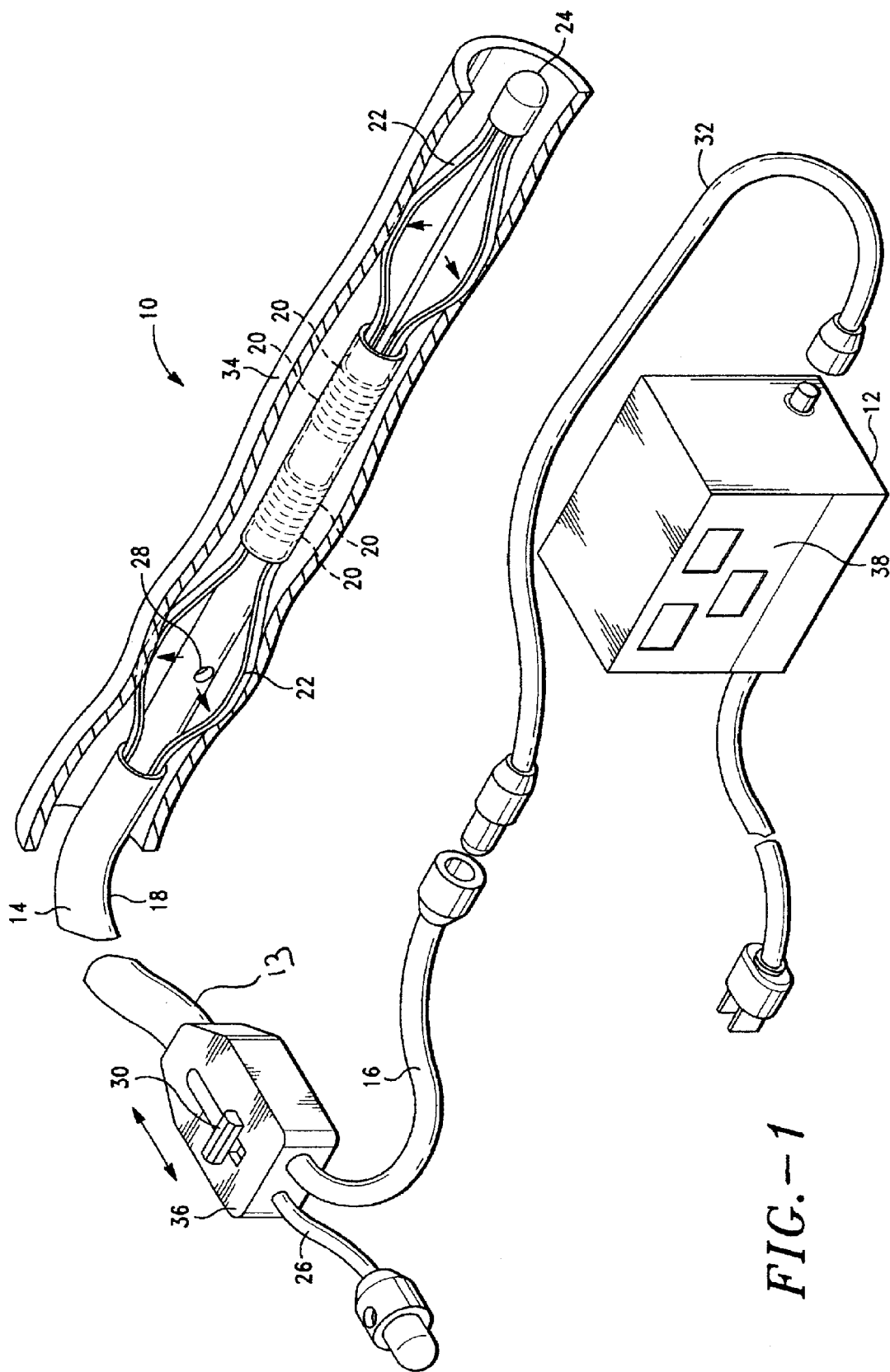
FIG. 1 is a perspective view of a system in accordance with the present invention.

FIG. 1 shows a radio frequency patient heating system generally designated with the reference numeral 10. The heating system 10 includes a control unit 12 and a catheter generally designated with the reference numeral 13. The catheter 13 has a catheter body 14. The catheter body 14 has a proximal end 16, a distal end 18, deployable supports 22, a tip 24, an infusion lumen 26 with an ejection port 28, and a switch 30. The system 10 includes an electrical cable 32 connecting the control unit 12 and the catheter body 14.

The catheter body 14 includes a long (60 to 120 cm), thin (1 to 4 mm diameter, 3 to 12 French) cylindrical tube of a biocompatible polymer with stiffness balanced for flexibility and "push-ability".

The electrodes 20 mount on the distal end 18 of the catheter body 14. According to one aspect of the invention, the electrodes 20 comprise discrete bands that circumscribe the catheter body. The electrodes 20 are formed from a radiopaque alloy. Preferably, the electrodes are made from a platinum-iridium alloy or a stainless steel material. Fine conductors thread through the catheter body 14 to electronically couple the electrodes 20 via the distal end 16 of the catheter body 14 to the control unit 12.

During operation, and at any given moment, each electrode 20 has a polarity. For each electrode 20 there is an adjacent electrode having an opposite polarity. This creates an electric field between adjacent electrodes 20. The electric field is adapted to heat blood.

The infusion lumen 26 facilitates infusion of fluid such as medicine, nutrition, or contrast agent. Contrast agent infusion enables verification of (dye) in alignment and placement of the distal end 18 of the catheter body 14 within a blood vessel. The contrast agent injects via the infusion lumen 26 directly into flowing blood. The contrast agent exits the catheter body 14 via the ejection port 28, which is located on the distal end 18 of the catheter body 14 in a position proximal to the electrodes 20. It can be appreciated that fluids including medicinal fluids, blood thinners, etc. can be infused directly into the flowing blood via the infusion lumen 26.

The proximal end 16 of the catheter body 14 includes a handle 36. The handle 36 is used for holding and manipulating the catheter 13 during introduction, alignment and withdrawal of the catheter 13 from the patient. The handle 36 regulates contrast agent infusion according to one aspect of the invention.

The handle 36 houses the switch 30. The switch 30 mechanically couples with the supports 22. The switch 30 reciprocates to selectively deploy and retract the supports 22. According to an alternate embodiment, the supports 22 are automatically deployable and the switch 30 is not required.

The electrical cable 32 electronically connects the catheter body 14 to the control unit 12. The control unit 12 communicates power, temperature sensor feedback and other signals between the catheter 13 and an operator.

The control unit 12 includes an RF Power supply that couples to an alternating current source and converts typical AC current (e.g., 115 VAC/60 Hz US, 220 VAC/50 Hz Europe) into calibrated RF energy. Preferably, the RF energy is within the range of 100 kHz to 3,000 kHz, and more preferably, the RF energy is regulated at about 500 kHz.

The control unit 12 includes a control panel 38 to enable an operator to monitor the system 10 and to select a desired heating profile to administer. The control unit 12 enables an operator to verify system performance. The power supply also provides data acquisition capability to record the details of the voltage, current, power, impedance, flow rates and temperatures measured during the procedure.

According to an aspect of the invention, remotely deployed temperature sensors detect patient core body temperature and provide feedback to the control unit.

It is known that the electrical field density between adjacent electrodes 20 is the highest in the region between the electrodes, and the field extends radially (with respect to the catheter body 14) out from the electrodes 20 with decreasing intensity. The electric field warms the flowing blood. The flowing blood warms the distal end 18 of the catheter body 14 and with the electrodes 20.

The supports 22 position the electrodes 20, and the distal end 18 of the catheter body 14 centrally within the blood vessel 34. It can be appreciated that the term "centering" is loosely applied. It is preferable that the electrodes 20 are centered, not only with respect to a vascular axis, but also accounting for the position where the maximum blood flow rate through the blood vessel 34 is found. Accordingly, where the electrodes 20 and the catheter body 14 are coaxially aligned, as shown, "centering" positions the catheter body 18 where the blood flow rate is the highest, apart from the walls of the blood vessel 34.

It can be appreciated that variations of the invention may include electrodes that deploy in a non-coaxial arrangement with respect to the catheter body. In such embodiments, the electrodes are preferably centered within the blood vessel 34, while exact centering of the catheter body is not a necessity.

Any of a variety of devices can accomplish "centering" in accordance with the present invention. One way is through the use of the supports 22. Preferably, the supports 22 are thin and flexible wires. Even more preferably, the supports 22 are flattened to softly engage blood vessel walls. The supports 22 gently flex and a portion of each support 22 radially extends from the catheter body 14 to anchor the catheter body 14 centrally within the blood vessel 34. The supports 22 allow blood to flow through the vessel 34, between the supports 22 and the catheter body 14.

Figure 2A:
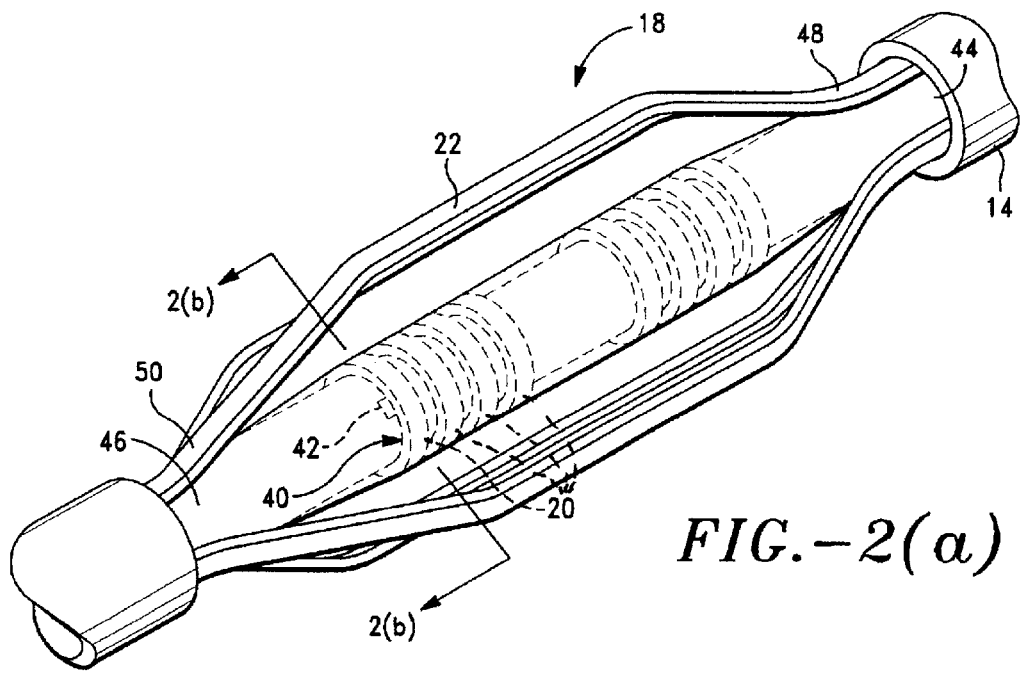
FIG. 2(a) is a perspective view of the distal end of a catheter body in accordance with the present invention.
Figure 2B:
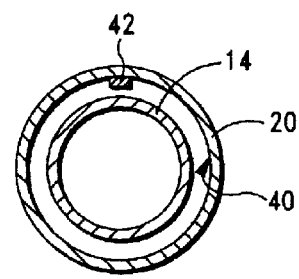
FIG. 2(b) is a cross-sectional view of the catheter body of FIG. 2(a) as seen along the line 2(b)—2(b).

FIG. 2(a) and FIG. 2(b) show an aspect of the invention having a sensor system with at least one temperature sensor element 42 fixed at the distal end 18 of the catheter body 14. Preferably, the sensor system has multiple temperature sensor elements 42 and one of the sensor elements 42 is positioned adjacent each electrode 20. The electrodes 20 define an inside 40, and according to one aspect of the invention, the sensor element 42 attaches to the inside 40 of each electrode 20. Each sensor element 42 preferably includes a thermocouple, but may include a thermistor or other device for detecting temperature in accordance another aspect of the invention.

It can be appreciated that in an alternate embodiment of the invention, the catheter body 14 includes a resistive, or a fluid based heating system that cooperates with the electrodes 20. In such an embodiment, the temperature sensors would optimally be positioned elsewhere. An example of a resistive heating system is disclosed in U.S. Pat. No. 6,149,673. An example of a fluid-based heating system is disclosed in U.S. Pat. No. 6,146,411. The disclosures of these patents are incorporated herein by reference.

It can be also appreciated that the sensor system of the present invention can be equipped with a pressure transducer attached to the distal end 18 of the catheter body 14 to facilitate measurement of the linear and volumetric blood flow rates within the blood vessel 34 (FIG. 1).

The control unit 12 (FIG. 1) monitors the electrodes 20 and sensor system impedances to verify functionality of those components. Should those measured impedances be out of established limits, the control unit provides an alarm.

FIG. 2(a) shows the supports 22 having two visually definable ends 48 and 50 in contact, respectively, with the distal end 18 of the catheter body 14. The end 48 slideably attaches to the catheter body 14 at a first position 44 proximal the electrodes 20. The end 50 slideably attaches to the catheter body 14 and at a second position 46 distal the electrodes 20. While the ends 48 and 50 are visually definable, the supports 22 extend within the catheter body 14 and terminate at the switch 30 (FIG. 1). The switch 30 selectively retracts the supports 22 to cause the supports 22 to lie flush with the exterior of the catheter body 14 during insertion and removal of the catheter body 14.

Figure 3:
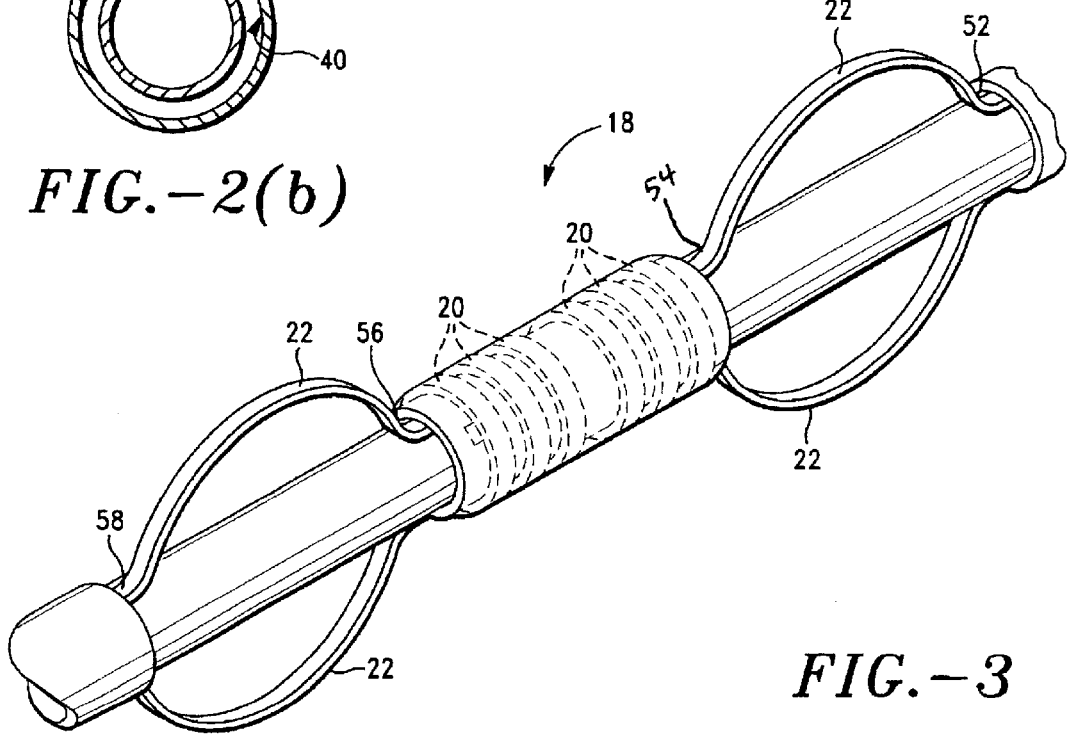
FIG. 3 is a perspective view of an embodiment of the distal end of a catheter body in accordance with the present invention.
Figure 4:
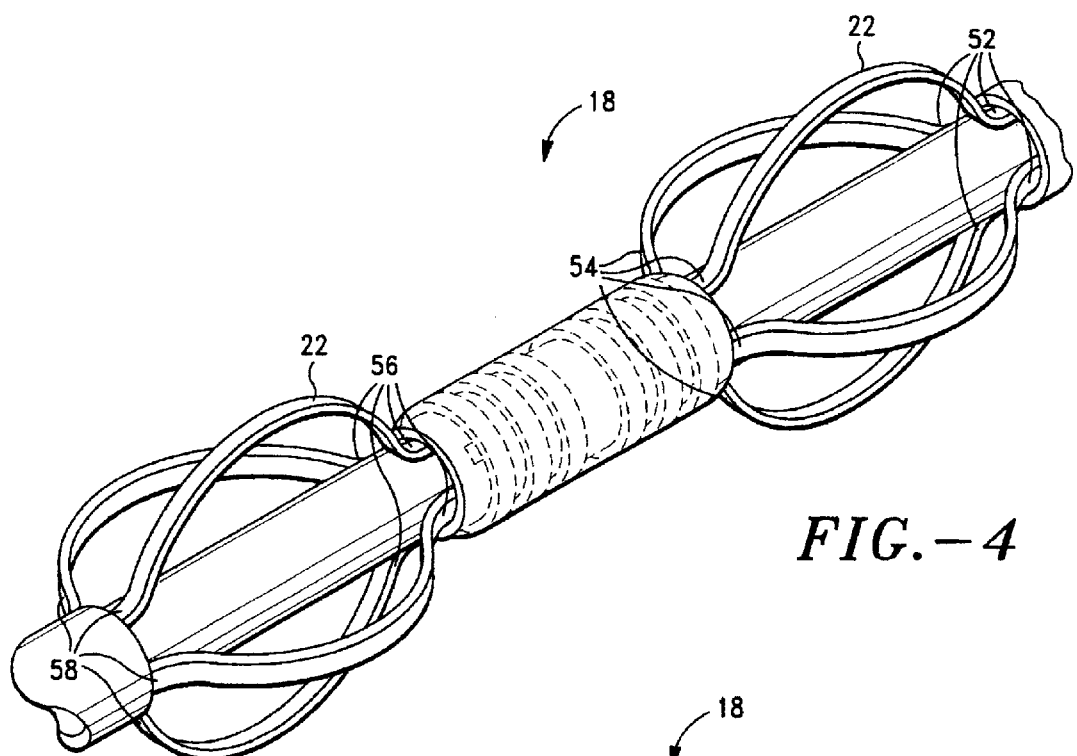
FIG. 4 is a perspective view of an embodiment of the distal end of a catheter body in accordance with the present invention.

FIG. 3 shows the distal end 18 having two pairs of supports 22 extending from the catheter body 14 in a coplanar arrangement. One pair of supports 22 has visually definable ends 52 and 54 that lie flush with the catheter body 14 in a position proximal to the electrodes 20 when the supports 22 deploy. The other pair of supports 22 has visually definable ends 56 and 58 that lie flush with the catheter body 14 in a position distal to the electrodes 20 when the supports deploy. FIG. 4 shows the distal end 18 having two groups of supports 22. One group of supports 22 has visually definable ends 52 and 54 that lie flush with the catheter body 14 in a position proximal to the electrodes 20. The other group of supports 22 has visually definable ends 56 and 58 that lie flush with the catheter body 14 in a position distal to the electrodes 20.

Figure 5:
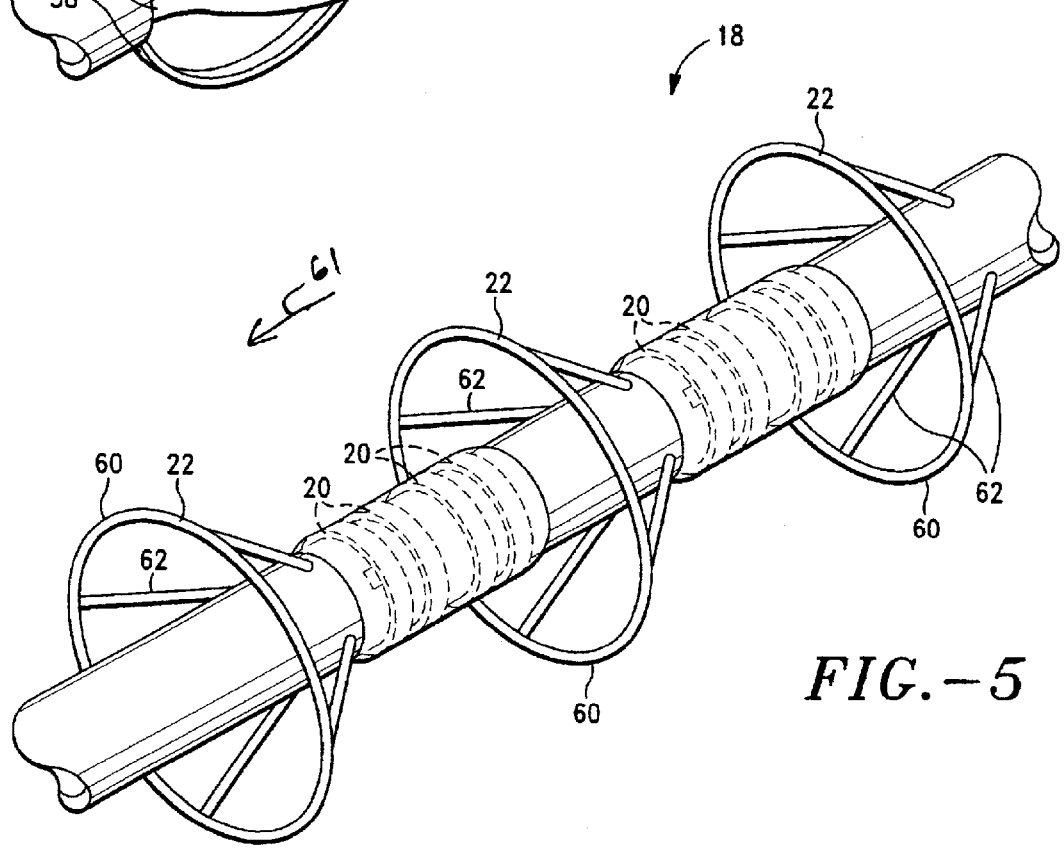
FIG. 5 is a perspective view of an embodiment of the distal end of a catheter body in accordance with the present invention.

FIG. 5 shows the distal end 18 having supports 22. Each support includes a ring 60 and extensions 62. The extensions 62 mechanically couple with the switch 30 and support the ring 60 to selectively deploy the ring 60 against the blood vessel 34 (FIG. 1). The supports 22 form a frustum shape when deployed to facilitate blood flow between the rings 60 and the surface of the distal end 18.

It can be appreciated that the rings 60 and the extensions 62 can be configured for directing blood towards the electrodes 20. Blood flows in the direction of the arrow 61.

According to one aspect of the invention, an insertion tube surrounds the catheter to hold the supports 22 flush with the distal end of the catheter body. Once the catheter body inserts into the patient, the insertion tube withdraws to allow the supports 22 to automatically deploy. Thus the switch 30 is not required.

Figure 6:
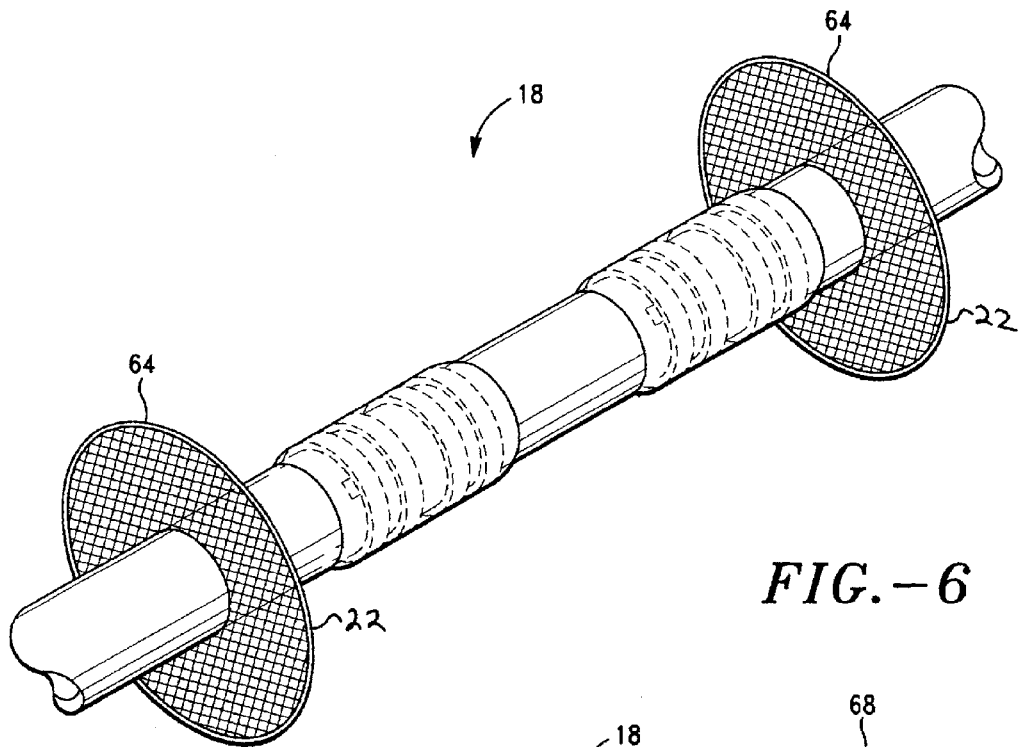
FIG. 6 is a perspective view of an embodiment of the distal end of a catheter body in accordance with the present invention.

FIG. 6 shows the distal end 18 having supports 22. The supports 22 each comprise an annular web 64. Blood flows through the web 64. In accordance with one aspect of the invention, the web 64 is fabricated from a conductive material that the control unit 12 (FIG. 1) resistively heats to warm the blood as the blood flows through the web 64. Each web 64 forms a frustum shape in accordance with an alternate embodiment of the invention.

Figure 7:
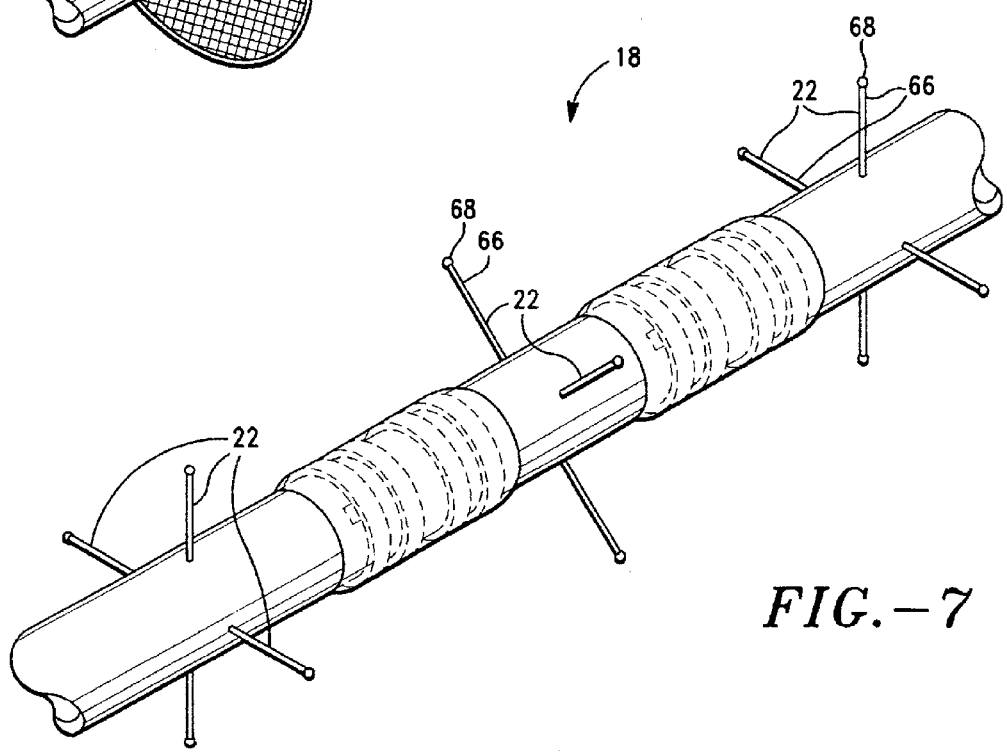
FIG. 7 is a perspective view of an embodiment of the distal end of a catheter body in accordance with the present invention.

FIG. 7 shows the distal end 18 having supports 22. The supports 22 each include pins 66 that extend radially from the distal end 18. The pins 66 are formed from a pliable material that gently centers the distal end 18 within a blood vessel. Each pin 66 includes a soft tip 68.

It can be appreciated that although the pins 66 deploy radially with respect to the catheter body 18, that the pins 66 can also deploy at an oblique angle from the catheter body 18.

Figure 8:
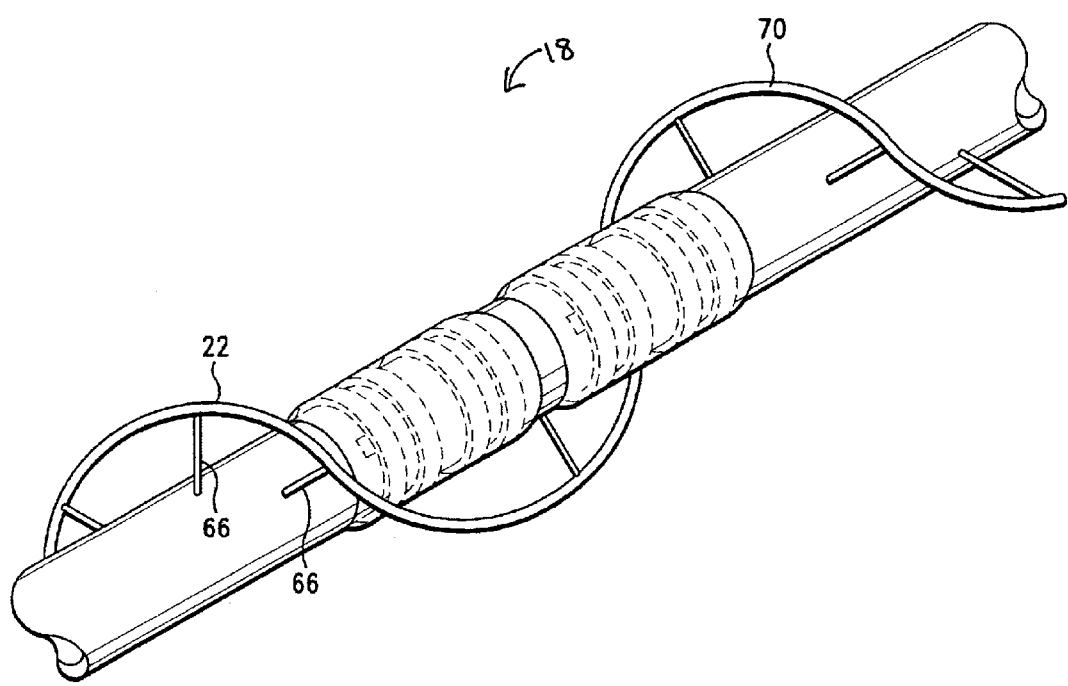
FIG. 8 is a perspective view of an embodiment of the distal end of a catheter body in accordance with the present invention.

FIG. 8 shows the distal end having a single support 22. The support 22 includes multiple pins 66 extending from the surface of the distal end 18. The pins 66 align in a helix. The support 22 includes a helical wire 70 that interconnects the pins 66 and provides a helical surface for contacting the blood vessel walls. The pins 66 are mechanically coupled with the switch 30 (FIG. 1) to effectuate selective deployment of the support 22.

In Operation

During normal operation, the control unit 12 monitors signal generated by the sensor system, including the temperature sensor elements 42, any pressure sensor, or any remote temperature sensor. The control unit 12 automatically increases or decreases the current and voltage as required to achieve a desired core body temperature. The control unit 12 continually monitors the impedance of the electrodes (and/or phase angle between the voltage and current) as a measure of the system performance and safety. To illustrate, should the impedance shows a sudden rise, this could indicate that an adherent coagulum and/or protein deposition has manifest on the electrodes. As this condition is detected, the power level automatically decreases, or ceases, to prevent damage to the blood.

The system 10 includes a percutaneous introducer set. The introducer set preferably includes a short introducing catheter with a hemostat valve, a large bore needle, a short introducing wire, and a dilator. In operation, the needle pushes via the skin into the vessel. The introducing wire slides into the vessel, and the needle is withdrawn. The dilator and introducing catheter track over the introducing wire, through the muscle, into the vessel 34, or into an ancillary vessel such as the femoral artery. Removal of the introducing wire and dilator enables the introducing catheter and hemostat to provide access to the vasculature. When catheter body 14 inserts into the vessel 34, the hemostat prevents blood loss.

The Electric Field

The electrodes 20 create an electric field substantially parallel to the catheter body 14. This electric field can be visualized as a hollow cylinder (an annulus) representing a zone of influence that circumscribes the distal end 18 of the catheter body 14. This electric field represents the sum of the electric fields created by the electrodes 20. The zone of influence affect blood flowing past the catheter within the bounds of the zone of influence.

In general, the heating of any incremental volume element of blood can be expressed as the time integral of the field power that the blood experiences over its path through the zone of influence. The (time and location varying) instantaneous power can be expressed as the local current squared times the total resistance of that volume element. Note that the current density will not typically be a constant value, and will, in general, decrease approximately as the square of the distance from the electrode 20. Therefore, the heating of any given volume element will be approximately proportional to the fourth power of the distance of that element from the nearest electrode 20. Note also that the temperature rise of any given volume element will be dependent principally on the following three factors, the distance from the electrode 20, the flow rate of the blood, and the total current passing through the electrodes.

The blood temperature at any given moment will be generally highest at or immediately adjacent to the electrodes. The blood temperature decreases at further distances. Placement of temperature sensors elements 42 on, or immediately adjacent to, the electrodes 20 property permits the monitoring and control of the highest blood temperatures by the system 10.

The present invention is described by way of example only. There are many viable embodiments of this invention. For example, the supports 22 can be fabricated in any way that allows blood flow between the catheter 13 and the supports 22 in order to heat the blood. The catheter 13 may be warmed by alternate means. The supports 22 can also be warmed. The electrodes 20 can be replaced with any viable radiative heating element. Furthermore, the supports 22 may have a variety of shapes and configurations other than those disclosed. Accordingly, the invention is to be limited only by the claims as set forth below.

What is claimed is:

1. A heat exchange catheter for warming blood within a blood vessel comprising:
  a catheter body having a proximal end and a distal end;
  electrodes on the distal end of the catheter body for generating an electric field that radiates heat to the blood; and
  a means for positioning the distal end centrally within the blood vessel,
  wherein the positioning means includes supports having pins that radially extend from the catheter body to bear gently against the blood vessel.

2. A heat exchange catheter for warming blood within a blood vessel comprising:
  a catheter body having a proximal end and a distal end;
  electrodes on the distal end of the catheter body for generating an electric field that radiates heat to the blood; and
  a means for positioning the distal end centrally within the blood vessel, wherein the positioning means includes supports, each support includes a ring and extensions, the extensions support the ring selectively deploy the ring against the blood vessel.

3. A heat exchange catheter for warming blood within a blood vessel comprising:

a catheter body having a proximal end and a distal end;

electrodes on the distal end of the catheter body for generating an electric field that radiates heat to the blood; and a means for positioning the distal end centrally within the blood vessel, wherein the positioning means includes a web.

4. A heat exchange catheter for warming blood within a blood vessel having a wall, the heat exchange catheter comprising:

a catheter body having a proximal end and a distal end;

electrodes on the distal end of the catheter body for generating an electric field that radiates heat to the blood; and a means for positioning the distal end centrally within the blood vessel, wherein the positioning means includes a helical wire for contacting a blood vessel wall along a helical path, the helical wire being distanced from the distal end of the catheter body to facilitate blood flow between the helical wire and the catheter body.

5. A heat exchange catheter for warming blood within a blood vessel comprising:

a catheter body having a proximal end and a distal end;

electrodes on the distal end of the catheter body for generating an electric field that radiates heat to the blood; and a means for positioning the distal end centrally within the blood vessel, wherein the positioning means includes a web that circumscribes the catheter body, the web being selectively deployable from a first configuration where the web lies on the catheter body, to a second configuration where the web extends from the catheter body to the blood vessel, the web permits blood to flow through the web when the web holds the catheter body centrally within the blood vessel.

6. A heat exchange catheter as set forth in claim 5, wherein the positioning means achieves a frustum shape in the second configuration.

* * * * *